(12) United States Patent
Ntziachristos et al.

(10) Patent No.: US 11,857,290 B2
(45) Date of Patent: Jan. 2, 2024

(54) DEVICE FOR ENDOSCOPIC OPTOACOUSTIC IMAGING, IN PARTICULAR FOR ENDOSCOPIC OPTOACOUSTIC IMAGING OF CAVITIES AND HOLLOW OBJECTS

(71) Applicant: Helmholtz Zentrum Munchen Deutsches Forschungszentrum Für Gesundheit Und Umwelt (GmbH), Neuherberg (DE)

(72) Inventors: Vasilis Ntziachristos, Munich (DE); George Sergiadis, Peraia (DE); Christian Zakian, Manchester (GB); Andreas Buehler, Neuherberg (DE)

(73) Assignee: Helmholtz Zentrum Munchen Deutsches Forschungszentrum Fur Gesundheit und Umwelt (GmbH), Neuherberg (DE)

( * ) Notice: Subject to any disclaimer, the term of this patent is extended or adjusted under 35 U.S.C. 154(b) by 524 days.

(21) Appl. No.: 16/638,983

(22) PCT Filed: Aug. 14, 2018

(86) PCT No.: PCT/EP2018/071979
§ 371 (c)(1),
(2) Date: Feb. 13, 2020

(87) PCT Pub. No.: WO2019/034633
PCT Pub. Date: Feb. 21, 2019

(65) Prior Publication Data
US 2020/0196873 A1    Jun. 25, 2020

(30) Foreign Application Priority Data
Aug. 16, 2017  (EP) .................................. 17186394

(51) Int. Cl.
*A61B 5/00* (2006.01)
*A61B 1/04* (2006.01)
(Continued)

(52) U.S. Cl.
CPC ............ *A61B 5/0095* (2013.01); *A61B 1/041* (2013.01); *A61B 1/00147* (2013.01);
(Continued)

(58) Field of Classification Search
None
See application file for complete search history.

(56) References Cited

U.S. PATENT DOCUMENTS

| 4,901,578 A * | 2/1990 | Brill, III ............... F22B 37/003 73/623 |
| 2010/0280504 A1 | 11/2010 | Manzke et al. |

(Continued)

FOREIGN PATENT DOCUMENTS

JP    2013022171 A    2/2013

OTHER PUBLICATIONS

International Search Report and Written Opinion dated Dec. 3, 2018 for PCT/EP2018/071979.

(Continued)

*Primary Examiner* — Christopher Koharski
*Assistant Examiner* — Michael S Kellogg
(74) *Attorney, Agent, or Firm* — Dorsey & Whitney LLP

(57) ABSTRACT

The invention relates to a device (1) for endoscopic optoacoustic imaging comprising an imaging unit (2) configured to be at least partially inserted into an object (5), said imaging unit (2) comprising an irradiation unit (6) configured to irradiate a region of interest (7) inside the object (5) with electromagnetic radiation and a detection unit (8) comprising at least one ultrasound transducer configured to detect ultrasound waves generated in the region of interest (Continued)

Figure 1:
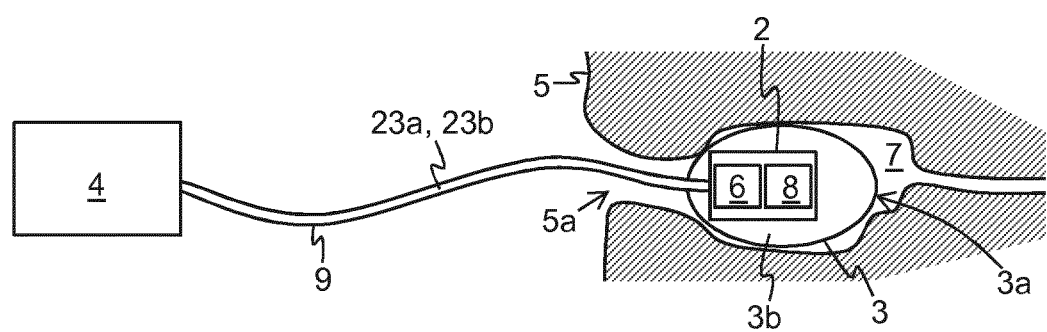

(7) in response to irradiating the region of interest (7) with the electromagnetic radiation and to generate according detection signals, wherein the at least one ultrasound transducer exhibits a field of view (8b) being at least partially located in the irradiated region of interest (7). A position stabilizing structure (3) with an outer face (3a) and an interior (3b) is configured to stabilize and/or fix the imaging unit (2) in a position and/or orientation in the object (5) by bringing the outer face (3a) of the position stabilizing structure (3) into contact with the object (5). The device (1) further comprises a processing unit (4) configured to generate an optoacoustic image (23b) of the region of interest (7) based on the detection signals.

14 Claims, 7 Drawing Sheets

(51) Int. Cl.
*A61B 1/00* (2006.01)
*A61B 8/12* (2006.01)
(52) U.S. Cl.
CPC ....... *A61B 1/00148* (2022.02); *A61B 1/00165* (2013.01); *A61B 5/0066* (2013.01); *A61B 5/0068* (2013.01); *A61B 5/0071* (2013.01); *A61B 5/0075* (2013.01); *A61B 5/6861* (2013.01); *A61B 8/12* (2013.01)

(56) References Cited

U.S. PATENT DOCUMENTS

| | | | |
|---|---|---|---|
| 2011/0275890 A1* | 11/2011 | Wang | A61B 8/4461 600/104 |
| 2013/0310643 A1* | 11/2013 | Gora | A61B 1/041 600/109 |
| 2015/0223698 A1* | 8/2015 | Subramaniam | A61B 5/0261 600/407 |
| 2015/0272445 A1* | 10/2015 | Rozental | A61B 1/00071 600/407 |
| 2016/0235305 A1 | 8/2016 | Wang et al. | |
| 2016/0242737 A1 | 8/2016 | Zhou | |

OTHER PUBLICATIONS

Yang, et al., Catheter-Based Photoacoustic Endoscope, Journal of Biomedical Optics, vol. 19(6) ,Jun. 2014.
European Search Report dated Apr. 7, 2022 for EP18758841.3.

* cited by examiner

DEVICE FOR ENDOSCOPIC OPTOACOUSTIC IMAGING, IN PARTICULAR FOR ENDOSCOPIC OPTOACOUSTIC IMAGING OF CAVITIES AND HOLLOW OBJECTS

This patent application is a U.S. National Stage filing under 35 U.S.C. 371 of International Patent Application No. PCT/EP2018/071979 entitled "DEVICE FOR ENDOSCOPIC OPTOACOUSTIC IMAGING, IN PARTICULAR FOR ENDOSCOPIC OPTOACOUSTIC IMAGING OF CAVITIES AND HOLLOW OBJECTS," filed Aug. 14, 2018, which claims priority to European Patent Application No. 17186394.7, filed Aug. 16, 2017, each of which is incorporated herein by reference in its entirety.

The present invention relates to a device for endoscopic optoacoustic imaging, in particular for endoscopic optoacoustic imaging of cavities and hollow objects, according to the independent claim.

Endoscopy is a standard technique for examination of the gastrointestinal (GI) tract and based on a flexible imaging probe, e.g. an optical video endoscope, inserted through a natural orifice, e.g. into the digestive system, for visual inspection of the luminal organ of interest. However, it is often impossible to detecting early disease by visual perception, which lacks specificity and staging ability. It is also limited to superficial structures. Thus disease-related features manifested below the tissue surface, e.g. possible infiltration of the gastrointestinal wall by precancerous and cancerous lesions or metastatic invasion of the adjacent lymph nodes, cannot be revealed. For diagnostic purposes the gastroenterologist has to extract a tissue biopsy from the suspect region which is examined by a pathologist under a microscope to render the final diagnosis. Unfortunately, a biopsy represents only a fractional area of tissue, thus it can easily miss disease, typically manifested as microscopic and/or biochemical changes.

To improve diagnostic accuracy, a class of imaging technologies capable of providing optical biopsies in living patients without excising any tissue has been provided. Among them are confocal laser endomicroscopy and optical coherence tomography (OCT). OCT endoscopes exist in form of catheters insertable via the working channel of a video endoscope and in form of a rigid swallowable tethered capsule to maximize patient comfort. Yet, OCT suffers from an inherent lack of molecular contrast (the ability to distinguish a molecule of interest from others). Also the gastrointestinal wall is generally thick and cannot be covered completely by OCT. Accordingly, there may be a need to address at least some of the above-described deficiencies.

Optoacoustic signal generation is based on the photoacoustic effect, according to which ultrasonic waves are generated due to absorption of electromagnetic radiation by an object, e.g. a biological tissue, and a subsequent thermoelastic expansion of the object. Excitation radiation, for example laser light or radiofrequency radiation, can be pulsed radiation or continuous radiation with varying amplitude or frequency.

It is an object of the invention to provide a device for endoscopic optoacoustic imaging, in particular endoscopic optoacoustic imaging of cavities and hollow objects, which is improved regarding image acquisition.

The object is achieved by a device for endoscopic optoacoustic imaging, in particular for endoscopic optoacoustic imaging of cavities and hollow objects, according to the independent claim.

The device according to an aspect of the invention comprises an imaging unit configured to be at least partially inserted into an object. The imaging unit comprises an irradiation unit configured to irradiate a region of interest inside the object with electromagnetic radiation and a detection unit comprising at least one ultrasound transducer configured to detect ultrasound waves generated in the region of interest in response to irradiating the region of interest with the electromagnetic radiation and to generate according detection signals, the at least one ultrasound transducer exhibiting a field of view being at least partially located in the irradiated region of interest. The device further comprises a position stabilizing structure with an outer face, in particular an outer surface, and an interior, in particular a hollow cavity, and being configured to stabilize and/or fix the imaging unit in a position and/or orientation in the object by bringing the outer face of the position stabilizing structure into contact with the object. The device further comprises a processing unit configured to generate an optoacoustic image of the region of interest based on the detection signals.

Preferably, the term "field of view" of the at least one ultrasound transducer relates to an area or a volume, from which the at least one ultrasound transducer is capable of detecting acoustic waves. In particular, the field of view may correspond to a solid angle originating at the at least one ultrasound transducer, inside of which the at least one ultrasound transducer is sensitive to ultrasonic waves. For example, the at least one ultrasound transducer may comprise at least one unfocussed ultrasound transducer configured to detect acoustic waves originating from within a cone-like or cylinder-like volume. In another example, the at least one ultrasound transducer may comprise at least one focused ultrasound transducer. In this case, the field of view comprises a focus point or focus region in which the sensitivity of the at least one transducer for acoustic waves exhibits a maximum.

A preferred aspect of the invention is based on the approach to provide an imaging unit which is dimensioned and/or formed such that it can be inserted into a cavity of an object, e.g. a human body, and to further provide a position stabilizing structure, which is preferably arranged at or close to the imaging unit and/or which preferably supports the imaging unit and which is configured to position and/or orient the imaging unit relative to a region of interest, e.g. an organ, inside the object. The imaging unit is configured to perform optoacoustic imaging of the region of interest of the object when and/or after being positioned and/or oriented.

Preferably, the position stabilizing structure is configured to be inserted into the object as well and, after having been inserted, to stabilize the imaging unit with respect to the region of interest by contacting an inner structure of the object, e.g. an inner wall of a hollow organ, with an outer face of the position stabilizing structure. In other words, the position stabilizing structure is configured to support the imaging unit on and/or against an inner structure of the object. Preferably, the position stabilizing structure is configured such that its outer face exerts a pressure onto the surrounding object to generate and/or increase friction between the outer face of the position stabilizing structure and the object such that the position stabilizing structure and hence the imaging unit are fixed and/or locked inside the object, in particular in a lumen of the object, at the region of interest due to increased friction forces. Alternatively or additionally, the position stabilizing structure may be configured such that its outer face assumes a size and/or shape which, at least partially, meshes with the shape and/or size of the surrounding structure of the object such that the position stabilizing structure and hence the imaging unit are fixed and/or locked inside the object at the region of interest at least partially due to form fit (positive locking).

By this means, the irradiation unit of the imaging unit can precisely irradiate the region of interest with electromagnetic radiation. Likewise, the at least one ultrasound transducer of the imaging unit can precisely detect ultrasound waves generated in the region of interest in response to an irradiation with electromagnetic radiation.

As a result, images reconstructed from detection signals generated by the at least one ultrasound detector exhibit high resolution and/or signal to noise ratio.

In summary, the invention provides a device for endoscopic optoacoustic imaging, in particular endoscopic optoacoustic imaging of cavities and hollow objects, which is improved regarding image acquisition.

In a preferred embodiment of the invention, the field of view of the at least one ultrasound transducer exhibits at least one focus being at least partially located in the irradiated region of interest.

Preferably, the at least one ultrasound transducer is shaped such that it can detect ultrasound waves from a detection volume of the tissue inside the field of view. The characteristics of this detection volume are defined by the particular arrangement and construction of the ultrasound unit. For example, the detection volume may have a cylindrical or conical shape.

Preferably, the at least one focused ultrasound transducer comprises a shaped active aperture and/or an acoustic lens to ensure that its at least one focus is located in the irradiated region of interest with particularly high precision.

In some embodiments, the detection unit comprises an array of ultrasound transducers, each of which contributes to the detection of acoustic waves from the detection volume. In this way, image resolution and/or signal to noise ratio is further enhanced.

According to a preferred embodiment of the invention, the irradiation unit is configured to focus the electromagnetic radiation, in particular by means of an optical lens, wherein the focus of the irradiation unit is disposed in the region of interest. Preferably, said focus of the irradiation unit exhibits smaller lateral dimensions than the field of view of the at least one ultrasound transducer. By this means, the generated optoacoustic image exhibits a high resolution determined by the lateral dimensions of the focus of the irradiation unit.

Alternatively, the region irradiated with the electromagnetic radiation, in particular said focus of the irradiation unit, exhibits larger lateral dimensions than the field of view, in particular the focus, of the at least one ultrasound transducer. By this means, the generated optoacoustic image exhibits a resolution determined by the lateral dimensions of the field of view, in particular the focus, of the at least one ultrasound transducer.

According to a preferred embodiment of the invention, the detection unit forms and/or comprises an opening through which the electromagnetic radiation can pass to irradiate the region of interest. Preferably, the irradiation unit or at least a part thereof is provided in or behind said opening. The opening can be, e.g., an aperture or hole provided in a single-element ultrasound transducer or can be formed, e.g., by an array of ultrasound transducers, in particular a circular array, or an opening in the active ultrasound material. By this means, the electromagnetic radiation irradiates a large part of the field of view of the at least one ultrasound transducer in a particularly uniform and reliable manner. By means of this confocal illumination of the region of interest the quality of the optoacoustic images, in particular the resolution and/or the signal to noise ratio thereof, is further enhanced.

In some embodiments, the irradiation unit may comprise an optical waveguide system configured to steer a beam of the electromagnetic radiation and enabling tissue illumination through a central opening of the detection unit such that confocal illumination is achieved. The tissue illumination can be employed with a parallel beam, a diverging beam or a focused beam of the electromagnetic radiation on or within the tissue surface, further enabling confocal illumination within the tissue in the region of interest. The adaptation of illumination allows for different imaging resolution and imaging characteristics which may be preferable in different applications of the inventive device.

Preferably, by providing the irradiation unit and the detection unit at the position stabilizing structure at a fixed position relative to each other and to the region of interest, e.g. the tissue surrounding the position stabilizing structure, the at least one ultrasound transducer can be positioned in the vicinity of the region of interest and can therefore directly detect the ultrasound waves emanating from the region of interest without phase changes in the ultrasound waves due to e.g. reflection of the ultrasound waves. Alternatively or additionally, the detection unit may be positioned close to the region of interest such that the ultrasound waves only propagate a short distance until detection. In each case, signal to noise ratio and/or resolution is further enhanced.

According to a preferred embodiment of the invention, the imaging unit is at least partially disposed in the interior of the position stabilizing structure. In other words, the outer face of the position stabilizing structure at least partially surrounds and/or encompasses the imaging unit. Preferably, the position stabilizing structure forms a housing for at least a part of the imaging unit. Accordingly, the position stabilizing structure may be referred to as a shell for the imaging unit, in particular the radiation unit and/or the detection unit, in particular the at least one ultrasound transducer. By this means, it is particularly easy to position and/or orient the imaging unit with respect to the region of interest by bringing the outer face of the position stabilizing structure into contact with the object.

For example, the position stabilizing structure is configured to form an at least partially oval shell around the imaging unit. By this means, the position stabilizing structure and the imaging unit inside the position stabilizing structure can be inserted into the object with particularly low resistance. Further, the outer face of the oval shell is shaped to come into contact and/or mesh with the object, for example walls of a lumen inside the object, and thereby stabilize and/or lock the imaging unit with respect to the region of interest. It is to be understood that when the position stabilizing structure is inserted into a lumen, e.g. a hollow organ such as the esophagus, colon, vascular structures or other body edifices, the position stabilizing structure may distend the entire hollow organ, whereby it preferably comes into contact with the entire circumference of the hollow organ, in particular at least partially over the length of the organ.

Preferably, the position stabilizing structure is configured to shield the imaging unit, in particular the irradiation unit and/or the detection unit, from the outside of the position stabilizing structure, i.e. from environmental effects such as fluids and/or substances dissolved therein, and/or physical effects as impacts. This is particularly advantageous when the device is deployed in polluted environments and/or if the imaging unit comprises sensitive and/or critically aligned optical components such as lenses or mirrors.

Moreover, the position stabilizing structure is preferably designed so that luminal organs will naturally constrict around it, e.g. when swallowed, thus helping to align the imaging unit inside the imaged lumen and positioning the imaging unit with minimal and constant distance to the wall of the imaged lumen, so that a longitudinal axis, i.e. an axis of rotational symmetry, of the position stabilizing structure and/or imaging unit is oriented substantially parallel to the axis of the lumen. Aligning the imaging unit inside the imaged lumen reduces motion artifacts, which in turn limit volumetric image formation capability and comprehensive visualization of the luminal organ of interest. Preferably, this alignment also achieves substantially perpendicular illumination and sound detection with respect to the wall of the lumen. Thus, high and comparable image quality around the lumen's circumference can be provided.

In another preferred embodiment of the invention, the position stabilizing structure is disposable and detachably mounted onto the imaging unit. By this means, the position stabilizing structure can be easily replaced, for example if damaged or contaminated. In particular, the position stabilizing structure and at least a part of the imaging unit can be inserted into the object under sterile conditions.

In yet another preferred embodiment of the invention, the device comprises a carrier unit disposed in the interior of the position stabilizing structure, wherein the irradiation unit and the detection unit are mounted on the carrier unit such that electromagnetic radiation emanating from the irradiation unit is directed towards the field of view, in particular the focus, of the at least one ultrasound transducer. In particular, the carrier unit is preferably configured to align the irradiation unit and the detection unit with respect to each other such that electromagnetic radiation emanating from the irradiation unit is directed towards the field of view of the at least one ultrasound transducer. Alternatively or additionally, the carrier unit is configured to position and/or align the irradiation unit and/or the detection unit along the longitudinal axis of the position stabilizing structure. Preferably, the carrier unit is configured to position the irradiation unit and/or detection unit in the center of the position stabilizing structure, in particular such that a distance between the object, in particular a wall of a lumen inside the object, and the detection unit, in particular at least one detection surface of the at least one ultrasound transducer, is constant for all orientations of the detection unit. Thereby, the region of interest can be irradiated in a substantially uniform manner with the electromagnetic radiation and the intensities of acoustic waves emitted from different areas in the region of interest can be reliably compared.

Preferably, the irradiation unit comprises at least one optical element, which is mounted on the carrier unit and/or configured to guide the electromagnetic radiation from the interior of the position stabilizing structure, in particular from inside of the carrier unit, towards the region of interest. Preferably, the at least one optical element is configured to guide the electromagnetic radiation along a longitudinal axis of the position stabilizing structure and to further guide the electromagnetic radiation, in particular from a region around the center of the position stabilizing structure, towards the region of interest, wherein the propagation direction of the electromagnetic radiation is changed by a predetermined angle, in particular approx. 90°. In some embodiments, the at least one optical element comprises a mirror and/or a prism and/or an optical fiber.

Preferably, the mirror is an optical, acoustic or hybrid optical-acoustic mirror and is employed to direct a beam of electromagnetic radiation and a beam of ultrasound. Further preferably, by means of one or more mirrors, the beam of electromagnetic radiation may be scanned within the position stabilizing structure so that irradiation of at least a part of the region of interest, in particular along a hollow organ, can be achieved without moving the irradiation unit.

In another preferred embodiment of the invention, at least one fiber combiner is provided, which preferably uses double cladding fibers and which is configured to guide, on the one hand, the electromagnetic irradiation for irradiation of the region of interest, in particular from a radiation source outside of the object to the imaging unit inside the object, and, on the other hand, electromagnetic radiation emanating from the region of interest, in particular reflected radiation and/or fluorescence radiation in response to an irradiation with the electromagnetic radiation, from the imaging unit inside the object to an optical detection unit, e.g. a camera or a photodetector such as a photodiode or similar, outside of the object. By this means, the irradiation unit may be utilized by at least two imaging modalities, i.e. the optoacoustic imaging modality and, e.g., an optical and/or fluorescence imaging modality, in particular at the same time.

In this embodiment, the imaging unit is utilized both to transmit and receive electromagnetic radiation, e.g. in order to detect fluorescence, either due to intrinsic tissue fluorochromes or due to the administration of external fluorescence agents which can be employed for sensitive and specific identification of small lesions. In this case the electromagnetic radiation acts as excitation light which is emitted into tissue. Preferably, this is the same radiation as employed for the optoacoustic excitation of the ultrasound waves. Fluorescence from the tissue may be collected with the same imaging unit and separated with appropriate filters. Fluorescence recorded from different positions from the region of interest, e.g. a wall of an organ, can be employed to form an image, either a diffuse fluorescence image or confocal image, wherein the characteristics of said image depend on the illumination specifics. In particular, the resolution increases when focusing the electromagnetic radiation or arranging confocal irradiation. Preferably, the optical detector is designed to record diffusive fluorescence photons, or perform confocal rejection of diffusive photons to further improve resolution.

In yet another preferred embodiment of the invention, the carrier unit is configured to be rotated and/or translated with respect to the position stabilizing structure, preferably around and/or along a rotational-translational axis, in particular a longitudinal axis of the position stabilizing structure, such that the region of interest is scanned by the field of view, in particular the focus, of the at least one ultrasound transducer upon a rotation and/or translation of the carrier unit with respect to the position stabilizing structure. Preferably, the carrier unit is configured to be rotated around the longitudinal axis of the position stabilizing structure. By this means, different areas of the region of interest can be irradiated in a substantially uniform manner and acoustic waves emanating from the region of interest under different angles may be detected reliably, such that at least two-dimensional optoacoustic images can be obtained from the detection signals.

Preferably, the carrier unit is configured to be rotated and/or translated manually or by means of a driving unit, e.g. a motor. For example, in some embodiments the device comprises a driving unit disposed at the carrier unit, in particular in the interior of the position stabilizing structure, e.g. at a proximal or distal end of the interior of the position stabilizing structure, and configured to rotate and/or translate the carrier unit. In particular, the driving unit is preferably configured to apply a torque, a pulling force and/or a pushing force to the carrier unit in order to control the movement and/or position of the carrier unit during optoacoustic or multimodal imaging.

By this means, the irradiation unit and the detection unit may be moved within the position stabilizing structure in order to perform a, in particular three-dimensional, scan of a hollow organ without moving the entire position stabilizing structure relative to the organ. In particular, a rotation and/or translation of the carrier unit allows for movement of the irradiation unit and detection unit perpendicular to an imaging axis.

Preferably, the at least one ultrasound transducer exhibits a sensitive surface, which is sensitive to ultrasound waves, and is mounted and/or arranged on the carrier unit such that the sensitive surface of the ultrasound transducer faces towards the region of interest inside the object, and/or the field of view of the at least one ultrasound transducer runs substantially perpendicularly to the rotational-translational axis, in particular the longitudinal axis of the position stabilizing structure. This embodiment allows for positioning and scanning the ultrasound transducer closer to the region of interest than with conventional devices.

In this way, the path and/or propagation time needed by ultrasound waves to propagate from the region of interest towards the detection surface can be reduced considerably allowing for a faster scanning of the object and higher signal-to-noise ratio (SNR).

Preferably, the at least one ultrasound transducer, in particular the sensitive surface of the ultrasound transducer, comprises an aperture, e.g. a hole, and/or a window section being at least partially transparent to electromagnetic radiation, wherein the irradiation unit or at least a part thereof is mounted and/or arranged on the carrier unit such that the electromagnetic radiation emanating from the irradiation unit at least partially passes through the aperture or window of the ultrasound transducer to irradiate the region of interest inside the object. This allows for a particular efficient stimulation and detection of ultrasound waves in or, respectively, from the region of interest.

In yet another preferred embodiment of the invention, the device comprises a first transmitting unit configured to transmit a torque and/or a force, in particular from the outside of the object, to the carrier unit such that the carrier unit is rotated and/or translated with respect to the position stabilizing structure. Thereby, the region of interest can be scanned in a predetermined pattern with the field of view of the detection unit.

Preferably, the first transmitting unit comprises a distal end and a proximal end, wherein the distal end is coupled to the carrier unit, and the proximal end is configured to receive the torque. For example, the device comprises a driving unit, e.g. an electric motor, which is located outside of the object and coupled to the torque transmitting unit. Alternatively, the device comprises means to manually apply the torque to the first transmitting unit, or the first transmitting unit is configured to be manually actuated at the proximal end. By means of these embodiments, the position and/or orientation of the irradiation unit and/or detection unit with respect to the object or the region of interest, and thereby the content of the optoacoustic images, can be controlled from outside of the object, e.g. by a physician operating the device.

In yet another preferred embodiment of the invention, the first transmitting unit is configured to transmit a torque to the carrier unit such that the carrier unit rotates at a rotation rate of at least 1 Hz, in particular of at least 10 Hz, with respect to the position stabilizing structure. By this means, optoacoustic images can be reliably acquired by the detection unit mounted on the carrier unit.

In some embodiments, it is advantageous if the first transmitting unit is configured to transmit a torque to the carrier unit such that the carrier unit rotates at a considerably higher rotation rate, preferably of at least 20 Hz, in particular of at least 100 Hz or at least 200 Hz. By this means, the imaging unit can also be used for additional imaging modalities. For example, the imaging unit may comprise an optical coherence tomography (OCT) equipment configured to generate optical coherence tomography detection signals upon detection of electromagnetic radiation emanating from the region of interest in response to the irradiation with the electromagnetic radiation, such that the processing unit can generate optical coherence tomography images of the region of interest based on the optical coherence tomography detection signals. Alternatively or additionally, the imaging unit may comprise an ultrasound imaging system, allowing for parallel optoacoustic and ultrasound imaging.

In yet another preferred embodiment of the invention, the position stabilizing structure comprises a first thread and the first transmitting unit comprises a second thread complementary to the first thread, and the first transmitting unit is rotatably mounted to the position stabilizing structure by means of the first thread and the second thread. By applying a torque to the first transmitting unit, the torque transmitting unit and thus the carrier unit are translated with respect to the stabilizing structure, preferably along the longitudinal axis of the position stabilizing structure. By that means, the carrier unit can be rotated and translated with respect to the position stabilizing structure in particular easy and reliable manner from outside of the object.

By means of the superposition of a translational and the rotational movement of the carrier unit, the imaging unit, i.e. the detection unit mounted on the carrier unit, is suited to perform so-called helical scanning. In particular, the field of view of the at least one ultrasound transducer moves through the region of interest along a pathway forming a helix, whereby three-dimensional acoustic images can be reconstructed from the obtained detection signals.

Alternatively or additionally, the device comprises a first transmitting unit configured to transmit a torque and/or force to the carrier unit such that the carrier unit is rotated around and/or translated along the rotational-translational axis with respect to the position stabilizing structure, and/or a driving unit, e.g. a motor, configured to rotate the carrier unit around and/or to translate the carrier unit along the rotational-translational axis with respect to the position stabilizing structure.

Preferably, the position stabilizing structure comprises a first thread and the first transmitting unit and/or the driving unit comprises a second thread which is complementary to the first thread and mechanically coupled with the carrier unit, wherein the first thread and the second thread are in thread engagement, so that by applying a torque to the first transmitting unit and/or by activating the driving unit, e.g. the motor, the second thread is rotated, whereby the carrier unit is rotated and translated simultaneously with respect to the position stabilizing structure, whereby the field of view of the at least one ultrasound transducer moves through the region of interest along a helical pathway. This allows, in a particularly simple and reliable manner, for a volumetric scanning of the interior of the object without moving the position stabilizing structure with respect to the object.

In yet another preferred embodiment of the invention, the device comprises a driving unit, e.g. an electric motor, disposed in the interior of the position stabilizing structure and configured to rotate the carrier unit around and/or to translate the carrier unit along the rotational-longitudinal axis, for example an axis of rotational symmetry and/or a longitudinal axis, of the position stabilizing structure with respect to the position stabilizing structure. In this embodiment, forces and/or torques can be directly and reliably applied the carrier unit. Further, a connection between the outside of the object and the imaging unit, for example a catheter, can be particularly thin because only electric signals to control the driving unit and/or the detection signals have to be relayed through the connection.

In this embodiment, power may be delivered to the driving unit internally by a battery, which is preferably comprised by and/or located within the position stabilizing structure. This is particularly advantageous if the position stabilizing structure is detachably mounted to the imaging unit, in particular to the carrier unit. Alternatively, power is delivered from a proximal to a distal end of the connection, for example a catheter, e.g. by means of conducting wires or co-axial wire mesh preferably disposed inside the catheter. Said conducting wires or co-axial wire mesh are preferably arranged in parallel to or around an optical fiber employed for relay of the electromagnetic radiation. Alternatively of additionally, metal cables or wiring can be employed for transmitting power, providing stability and further protection of the optical fiber and the catheter.

Preferably, the position stabilizing structure further comprises an, in particular rigid, proximal end structure and an, in particular rigid, distal end structure, wherein the proximal end structure and the distal end structure are arranged along the longitudinal axis of the position stabilizing structure, and the driving unit is disposed at or in the region of the proximal end structure in the interior of the position stabilizing structure. Providing the drive unit, e.g. an electrical motor, at the proximal end of the position stabilizing structure has the advantage that conducting wires for electrical power supply of the drive unit have to be laid only up to the proximal end of the position stabilizing structure, making wires running through the position stabilizing structure, in particular through a region where the imaging unit is positioned and/or towards the distal end of the position stabilizing structure, dispensable. This allows for a stable full 360° rotational scan of the imaging unit which is not disturbed and/or adversely affected by conducting wires crossing the position stabilizing structure and/or the field of view of the imaging unit.

In yet another preferred embodiment of the invention, the irradiation unit comprises a radiation source configured to generate electromagnetic radiation, and a reflection element configured to reflect the electromagnetic radiation emanating from the radiation source towards the region of interest. For example, the irradiation unit may comprise a light emitting diode and/or a laser diode configured to emit the electromagnetic radiation along the longitudinal axis of the position stabilizing structure, such that a mirror disposed at the longitudinal axis reflects electromagnetic radiation towards the region of interest, in particular in a direction perpendicular to the longitudinal axis. In this embodiment, the radiation source may be mounted on the position stabilizing structure, while the reflection element may be mounted on the carrier unit. By this means, it is particularly easy to control the irradiation unit to irradiate the region of interest with the electromagnetic radiation.

In yet another preferred embodiment of the invention, the interior of the position stabilizing structure is configured to be filled with a coupling medium, preferably a medium which can couple ultrasound waves from the at least one ultrasound transducer to the region of interest and vice versa. Preferably, the medium is water, heavy water, oil, gel, polymer, for example polyurethanes, polyols and the like, or water-based hydrogel. By this means, the acoustic waves generated in the region of interest can travel to the detection unit without being substantially refracted, reflected or absorbed, such that particularly high signal to noise ratio can be achieved and spatial information is conserved. Preferably, the coupling medium is designed to lubricate the carrier unit, facilitating rotation of the carrier unit inside the position stabilizing structure. Preferably, the coupling medium is further designed to prevent the generation of air bubbles.

To allow multimodal imaging, the coupling medium preferably is designed to transmit radiation of different wavelengths. Therefore, in some embodiments the coupling medium is compatible both for ultrasound propagation and optical propagation, constituting an optical and ultrasound coupling medium (OUCM). A preferred optical feature of OUCM is that it exhibits no or only low attenuation and no or only little scattering in the wavelengths of electromagnetic radiation employed. Ultrasound waves from the at least one ultrasound transducer can be transmitted through the coupling medium to the tissue, and reflected ultrasound waves can be back-transmitted though the coupling medium to form ultrasound images. Further, the electromagnetic radiation, preferably comprising light of transient energy (photon pulses, intensity modulated light), is also transmitted through this coupling medium to the region of interest and generated ultrasound waves are back-transmitted through the coupling medium to the at least one ultrasound transducer. Alternatively or additionally, additional radiation, preferably at different wavelength, used in other possible hybrid implementations (OCT, fluorescence, CARS) is also coupled though this medium.

Preferably, the electromagnetic radiation and the ultrasound waves also couple through the position stabilizing structure, in particular its surface, enclosing the coupling medium as well as the irradiation unit and detection unit.

In yet another preferred embodiment of the invention, the position stabilizing structure comprises a membrane which is transparent for the electromagnetic radiation and/or the ultrasound waves. Preferably, the membrane is mechanically flexible and/or elastic.

Preferably, the position stabilizing structure further comprises a, in particular rigid, proximal end structure, e.g. a base, and a, in particular rigid, distal end structure, e.g. a cap, wherein the proximal structure and the distal structure are arranged along the longitudinal axis of the position stabilizing structure.

Preferably, the membrane is spanned between the proximal end structure and the distal end structure. Thereby, the membrane forms a hollow cylinder which is closed at the base by the proximal end structure and closed at the top by the distal end structure. Alternatively, the membrane can form a shell in which the irradiation unit and the detection unit are accommodated and which surrounds the irradiation unit and the detection unit in a substantially complete manner. By this means, a stable position stabilizing structure which can be easily inserted object can be provided.

Preferably, the membrane is configured to adapt its shape and/or size to the interior of the object, such that an outer face of the membrane assumes a size and/or shape which at least partially meshes with the shape and/or size of a surrounding structure in the interior of the object, whereby the position stabilizing structure is fixed and/or locked inside the object at least partially due to form fit (positive locking).

Preferably, the membrane is an elastic membrane configured to change its shape and/or size. In particular, the elastic membrane is configured to adapt its shape to the interior of the object, for example the walls of a lumen in the object, such that the object can be reliably contacted by the outer face of the position stabilizing structure.

Additionally or alternatively, the elastic membrane is configured to change its shape and/or size when coupling medium is filled into the position stabilizing structure or removed from the position stabilizing structure. Thereby, the position stabilizing structure can be easily inserted in the object in an empty state and reliably stabilize the imaging unit with respect to the region of interest in a filled state.

By increasing the shape and/or size of the position stabilizing structure, in particular by inflating the elastic membrane, improved interfacing of the coupling medium and the region of interest, e.g. the wall of an organ, can be achieved. This is particularly advantageous if the organ wall exhibits crypts, folds or a size that cannot be optimally distended by the position stabilizing structure. Preferably, the membrane acts as an inflatable balloon with adaptive dimensions, which generates additional stability compared to a thoroughly rigid position stabilizing structure enclosing the irradiation unit and the detection unit.

In yet another embodiment of the invention, the imaging unit comprises an optical sensor disposed in the interior of the position stabilizing structure and configured to acquire an, preferably optical, image of a region inside the object, e.g. the region of interest. Preferably, the optical sensor is configured to acquire the image by means of electromagnetic radiation emanating from the region of interest in response to the irradiation with the electromagnetic radiation, in particular reflected electromagnetic radiation. By this means, additional image information can be conveniently obtained from the region of interest.

For example, the optical sensor can be designed as a camera for acquiring conventional optical images or luminescence images of the region of interest. Alternatively or additionally, the optical sensor can be designed as part of an optical coherence tomography (OCT) equipment, multiphoton microscopy (MPM) equipment, fluorescence lifetime imaging (FLIM) equipment, shifted excitation Raman difference spectroscopy (SERDS) equipment or a coherent anti-Stokes Raman spectroscopy (CARS) equipment. By this means, functional imaging of the region of interest can be achieved in addition to optoacoustic imaging.

According to yet another preferred embodiment of the invention, the carrier unit comprises a first face and a second face opposite of the first face, wherein the illumination unit and the detection unit are mounted on the first face of the carrier unit and the optical sensor is mounted on the second face of the carrier unit. By this means, an optoacoustic image and a complementary additional image acquired by the optical sensor can be reliably acquired simultaneously. Preferably, a rotation of the carrier unit and the acquisition of the optoacoustic image and the complementary image are controlled, for example by the processing unit, in a way such that the optoacoustic image and the complementary image relate to the same area of the region of interest, i.e. the optoacoustic imaging of the complimentary image depicted the same features in the region of interest.

Alternatively, the optical sensor is mounted on a distal end of the carrier unit at the longitudinal axis of the position stabilizing structure, and a reflection element, for example a mirror, is mounted on the carrier unit at the longitudinal axis of the position stabilizing structure as well such that electromagnetic radiation emanating from the region of interest is reflected by the reflection element towards the optical sensor. In other words, the optical sensor and the reflection element are aligned along the longitudinal axis of the position stabilizing structure, which thereby defines an optical axis.

In yet another preferred embodiment of the invention, the device comprises an amplification unit disposed in the interior of the position stabilizing structure and configured to amplify the detection signals generated by the at least one ultrasound transducer. Accordingly, the amplification unit is arranged in the immediate neighborhood of the detection unit, such that the detection signals are amplified substantially immediately after their generation. By this means, loss of information contained in the detection signals due to attenuation of the signals over long distances can be avoided or at least reduced.

In yet another preferred embodiment of the invention, the device comprises at least one second transmitting unit comprising a proximal end and a distal end and configured to guide electromagnetic radiation and/or electrical signals from the proximal end to the distal end and/or from the distal end to the proximal end, wherein the imaging unit further comprises at least one rotational junction configured to optically and/or electrically couple the distal end of the second transmitting unit to the irradiation unit and/or to the detection unit. For example, the at least one second transmitting unit comprises wires for conveying electrical signals and/or radiation guides, e.g. one or more optical fibers, for conveying electromagnetic radiation. The at least one rotational junction can provide a connection between the rotationally mounted irradiation unit and/or detection unit and the, preferably stationary, second transmitting unit. By this means, the carrier unit or the imaging unit mounted thereon, respectively, may be rotated and/or translated, while the second transmitting element remains stationary, in particular with respect to the object. Preferably, the at least one second transmitting unit is configured to be arranged inside a catheter providing a connection to the imaging unit and/or the position stabilizing structure from outside the object. By this means, optoacoustic images can be reliably acquired inside the object, e.g. in a lumen of the object, and made available outside the object.

According to yet another preferred embodiment of the invention, the first transmitting unit and the second transmitting unit are separated from each other, in particular decoupled from each other. For example, the first transmitting unit and the second transmitting unit are guided through a catheter for providing a connection between the imaging unit and/or the position stabilizing structure and the outside of the object. In the catheter, the first and second transmitting unit are disposed alongside each other, a torque transmitted by the first transmitting unit is not imposed on the second transmitting unit. For example, when the second transmitting unit comprises one or more electrical wires and/or one or more optical fibers, a rotation of the first transmitting unit does not twist and/or move said electrical wires and/or optical fibers. By that means, no rotational fiber coupler to couple the second transmitting unit, in particular one or more optical fibers, to the irradiation unit is necessary.

Figure 2:
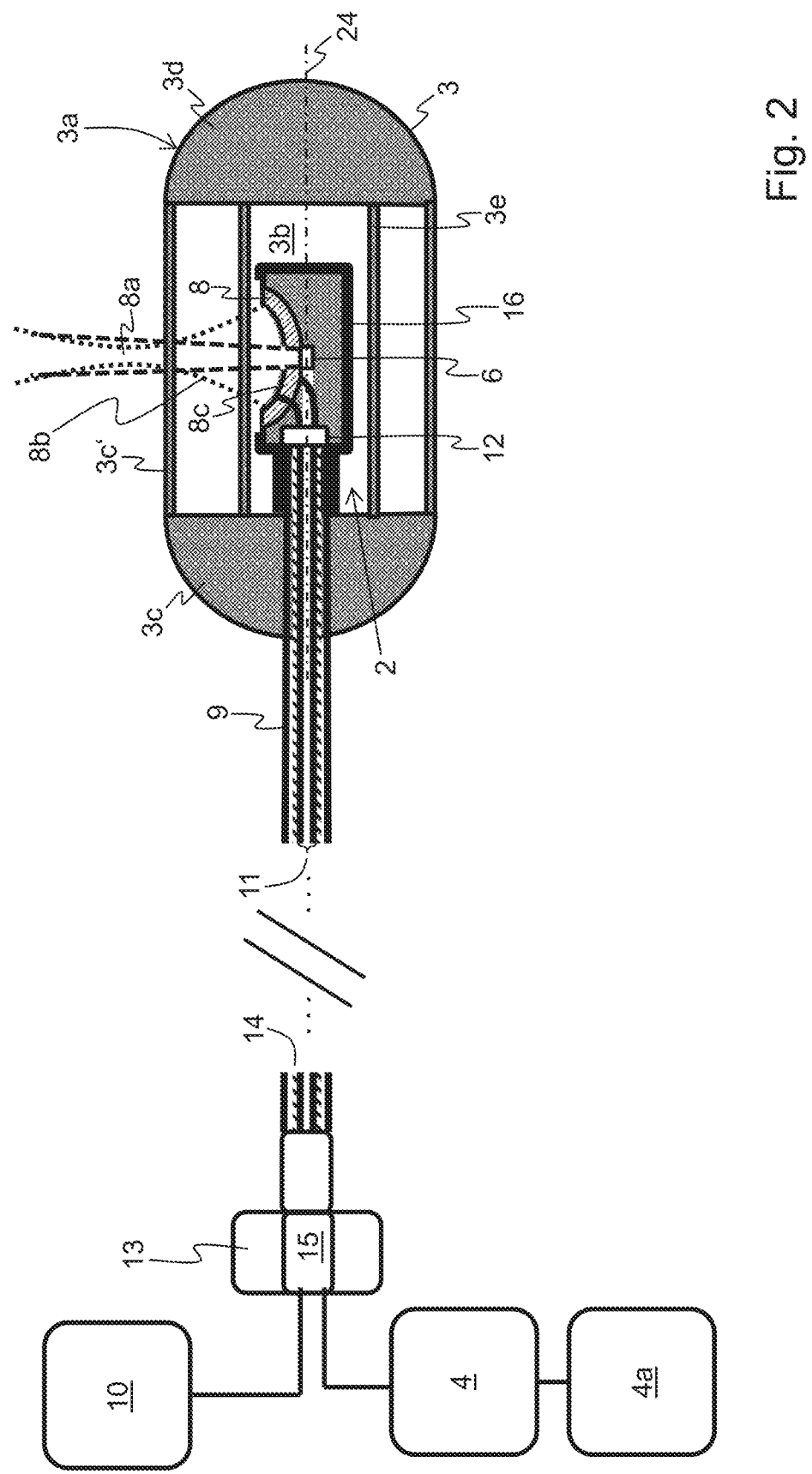
Figure 3:
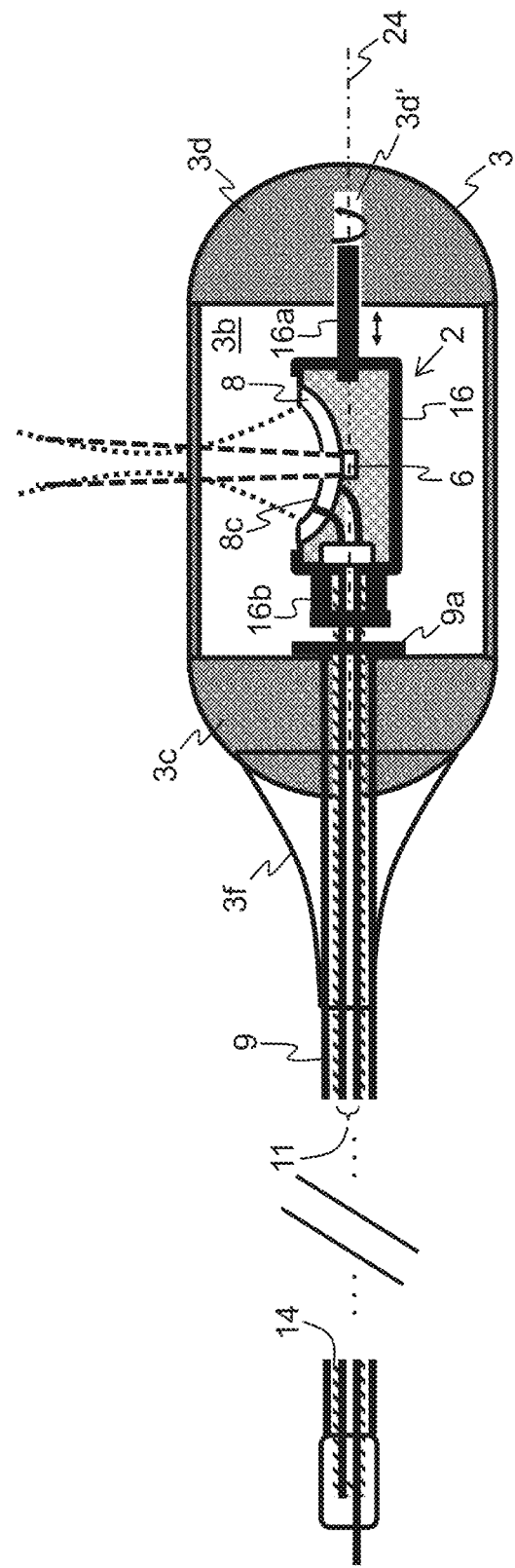
Figure 4:
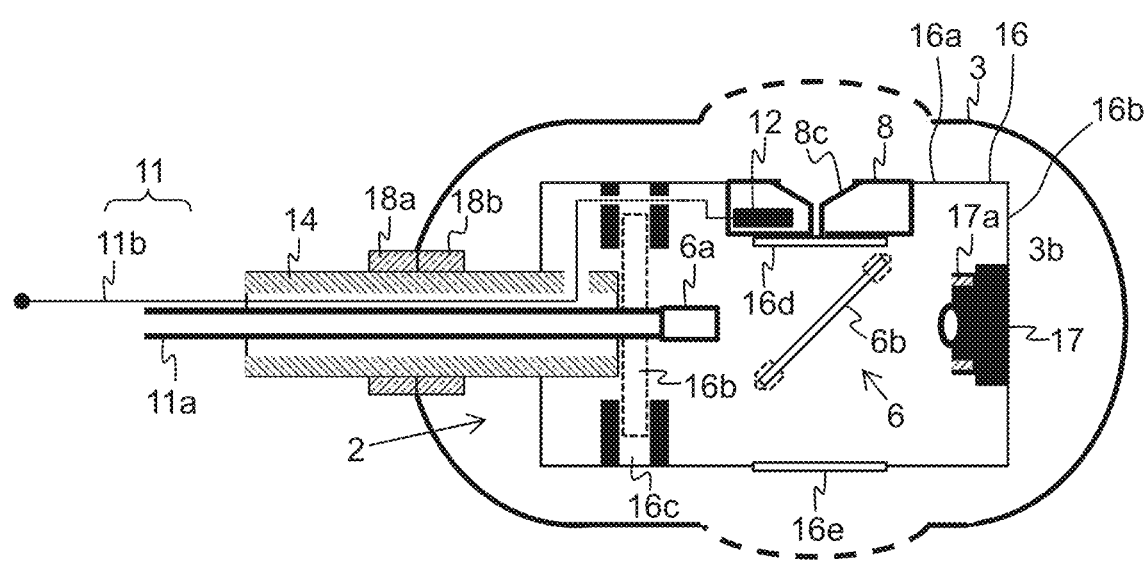
Figure 5:
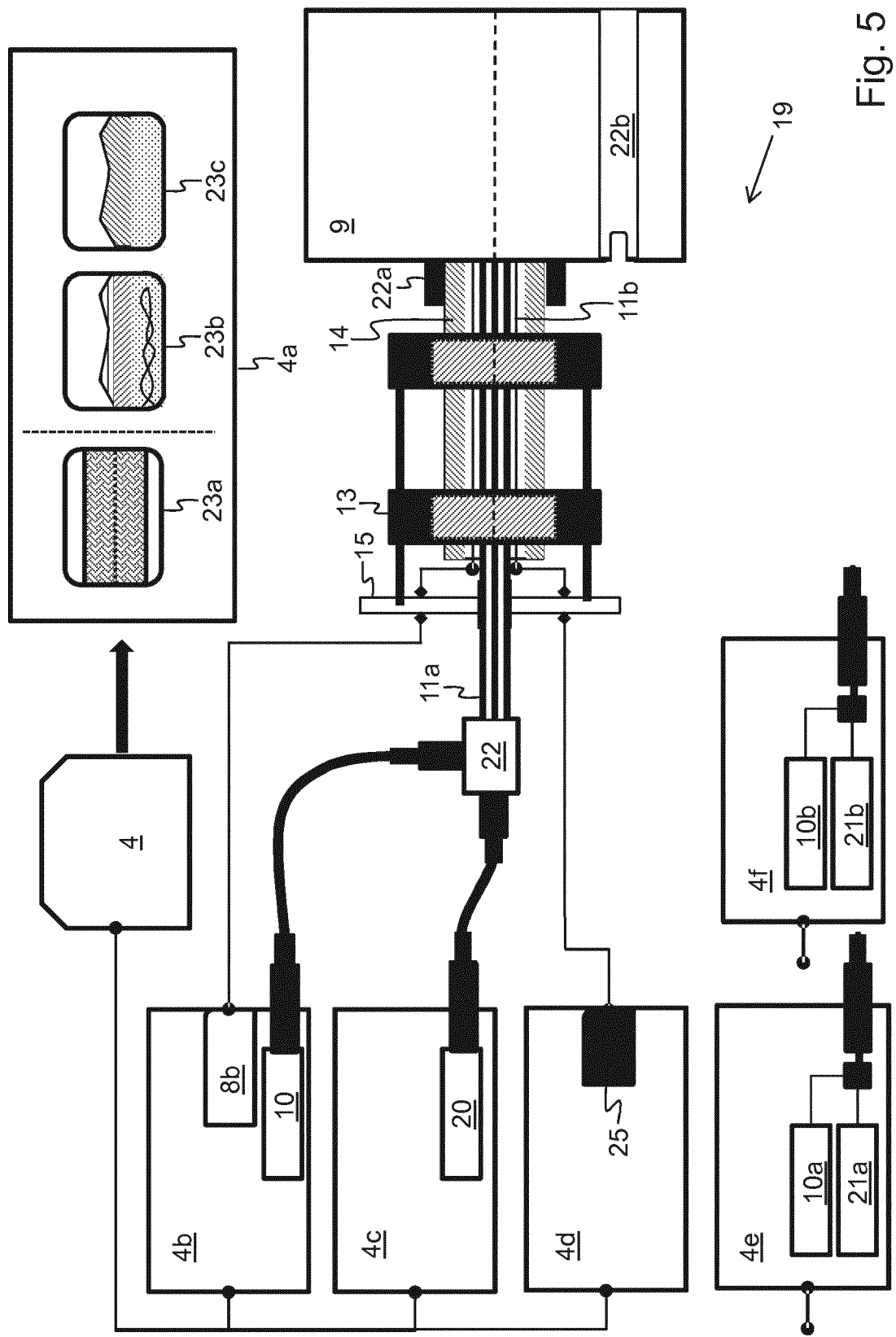
Figure 6:
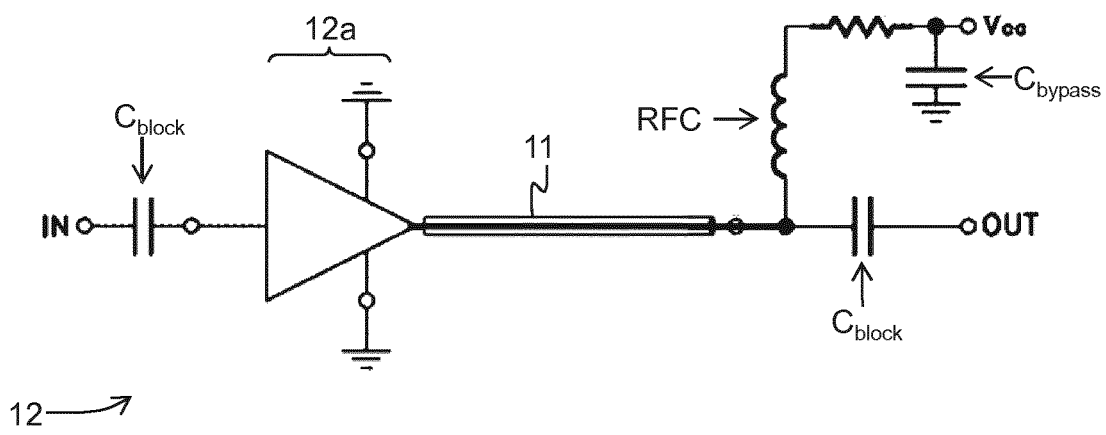

The above and other elements, features, characteristics and advantages of the present invention will become more apparent from the following detailed description of preferred embodiments with reference to the attached figures showing:

FIG. 1 an example of a device for endoscopic optoacoustic imaging;

FIG. 2 a first example of an imaging unit disposed in the interior of a position stabilizing structure;

FIG. 3 a second example of an imaging unit disposed in the interior of a position stabilizing structure;

FIG. 4 an example of a multimodal imaging unit;

FIG. 5 an example for a backend of a device for endoscopic optoacoustic imaging;

FIG. 6 an example of an amplification unit; and

Figure 7:
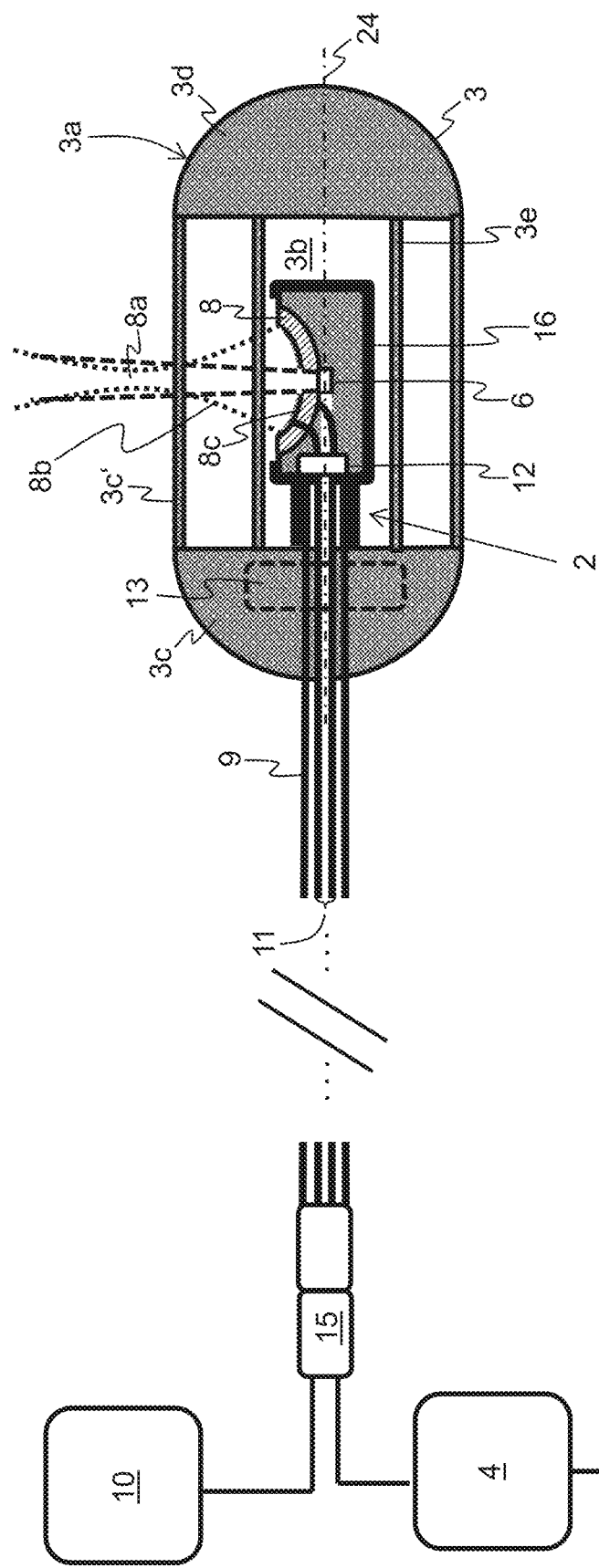

FIG. 7 another example of an imaging unit disposed in the interior of a position stabilizing structure.

FIG. 1 shows an example of a device 1 for endoscopic optoacoustic imaging comprising an imaging unit 2, a position stabilizing structure 3 and a processing unit 4. In the following, the position stabilizing structure 3 is also referred to as "position stabilizing unit".

The imaging unit 2 is configured to be inserted into an object 5, for example the gastrointestinal (GI) tract of the human, via a natural orifice 5a thereof, and comprises an irradiation unit 6 configured to irradiate a region of interest 7, for example the walls of a lumen inside the object 5, with electromagnetic radiation, in particular with light of a wavelength in the visible or infrared spectrum. Acoustic waves generated in the region of interest 7 in response to the irradiation with the electromagnetic radiation are detected by a detection unit 8, whereby according detection signals are generated.

The imaging unit 2 is connected to the processing unit 4 via a connecting element 9, for example a catheter. The processing unit 4 is configured to generate an optoacoustic image of the region of interest 7 based on the detection signals. Preferably, the processing unit is configured to control the irradiation unit 6 and hence the irradiation of the region of interest 7 with the electromagnetic radiation. Preferably, the connecting element 9 comprises a first channel 23a, e.g. electrical wires, configured to guide the detection signals from the imaging unit 2 provided at a distal end of the connecting element 9 to the processing unit 4 provided at a proximal end of the connecting element 9. Alternatively or additionally, the first channel 23a may be configured to guide electrical signals from the processing unit 4 to the irradiation unit 4 to control and/or to provide electrical power to the irradiation unit 4 for irradiating the region of interest 7 with electromagnetic radiation.

The position stabilizing structure 3 is arranged at the imaging unit 2, in particular at the distal end of the connecting element 9, and is preferably oval-shaped and/or elastically deformable to allow for an easy insertion through the orifice 5a of the object 5. In particular, the imaging unit 2 is disposed in the interior 3b, for example at the center, of the position stabilizing structure 3 such that the imaging unit 2 is surrounded by the position stabilizing structure 3. Because the imaging unit 2 is provided inside the surrounding position stabilizing structure 3, it can be—irrespective of its shape—easily brought to the region of interest 7 inside the object 5.

An outer face 3a of the position stabilizing unit 3 is configured to come into contact with the object 5, in particular at the region of interest 7, for example with walls of a lumen of the object 5, thereby stabilizing the imaging unit 2 in a position and/or orientation with respect to the region of interest 7.

Preferably, the size and/or shape of the position stabilizing unit 3 and/or the material and/or texture of the outer face 3a is or are configured such that the position stabilizing unit 3 is fixed and/or locked at a desired position relative to the region of interest 7 due to enhanced friction forces between the outer face 3a of the position stabilizing unit 3 and inner structures of the object 5 and/or due to form fit, i.e. positive locking between the position stabilizing unit 3 and inner structures of the object 5.

Preferably, the position stabilizing structure 3 is configured to be filled with a coupling medium for acoustically coupling at least one ultrasound transducer of the detection unit 8 with the region of interest 7. Preferably, the connecting element 9 comprises a second channel 23b configured to guide the coupling medium from outside of the object 5 into the interior 3b of the position stabilizing unit 3.

Preferably, the position stabilizing structure 3 comprises an elastic membrane configured to adapt its shape and/or size to the object 5 at the region of interest 7, in particular the walls of a lumen of the object 5.

For example, in an empty state, when no or only small amounts of coupling medium are present in the interior 3b, the position stabilizing structure 3 can be inserted into the object 5 and moved through the object 5, in particular through the GI tract, with low resistance. As soon as the region of interest 7 is reached, coupling medium can be filled into the position stabilizing structure 3 via the connecting element 9 such that the outer face 3a, in particular the membrane, comes into contact with the object 5 at the region of interest 7, thereby fixing the imaging unit 2 in a position and/or orientation relative to the region of interest 7.

By this means, optoacoustic imaging of the region of interest 7 can be performed by the imaging unit 2 without producing artifacts due to unintentional movement of the imaging unit 2 relative to the region of interest 7. In particular, by locking the position stabilizing structure 3 in the object 5 at the region of interest 7, a controlled alignment of the irradiation unit 6 and/or the detection unit 8, in particular with respect to region of interest 7, is achieved.

FIG. 2 shows a first example of an imaging unit 2 disposed inside a position stabilizing structure 3. In present example, the imaging unit 2 is coupled to connecting element 9 which connects the imaging unit 2, in particular detection unit 8 comprising at least one ultrasound transducer exhibiting a sensitive surface 8c being sensitive to ultrasound waves and irradiation unit 6, with processing unit 4 and radiation source 10, respectively. The irradiation unit 6 and the detection unit 8 together are also referred to as optoacoustic imaging head.

The position stabilizing structure 3 is located at a distal end of the connecting unit 9 and is configured to align and/or center a longitudinal axis of the optoacoustic imaging head inside an object at a region of interest, in particular in a lumen of the object. While, in present example, the position stabilizing structure 3 is substantially resistant to deformation, the connecting unit 9 is designed as a flexible tube, which is preferably configured to minimize stretching. Alternatively or additionally, the connecting unit 9 is designed to be resistant to rotational deformation. For example, the connecting unit 9 is a fabricated from dedicated plastics or a stainless steel flat wire coil or wire weave, coated on the outside with polyethylene, polyimide or Pebax® elastomers to assure smoothness and tear resistance.

The position stabilizing structure 3 has typically a larger diameter than the connecting element 9, such that luminal organs will constrict around it and thus stabilize and/or center the imaging unit 2 inside the lumen. For example, a diameter of the position stabilizing unit 3 at most 15 mm and a length of the position stabilizing unit 3 is at most 30 mm. When inside the luminal organ, the position stabilizing structure 3 will orient itself with its longitudinal axis 24 parallel to the axis of the lumen. Preferably, the diameter of the position stabilizing unit 3 is adapted to the imaged lumen. Thus for imaging different lumens, different position stabilizing structures 3 may be used. Typically, the position stabilizing structure 3 is rotationally symmetric with respect to its longitudinal axis 24. For example, the shape of the position stabilizing unit 3 resembles the form of a pill, facilitating swallowing of the position stabilizing unit 3. To ease the swallowing procedure, the position stabilizing structure 3 can be dipped in a fluid, such as water or saline, or coated on the outer face 3*a* with a coating lowering the friction coefficient.

The position stabilizing structure 3 preferably comprises a rigid or elastic shell with an outer face 3*a* that is at least optically and/or acoustically transparent and forms a cavity with an interior 3*b*. Thus, the interior 3*b* can be filled with a coupling medium, e.g. water, heavy water or mineral oil.

The position stabilizing structure 3 can comprise a proximal end 3*c*, in particular a base, with an imaging window portion 3*c*' and a distal end 3*d*, in particular a cap for sealing the position stabilizing structure 3. Sealing can be facilitated, for example, by permanent epoxying or using a snap connection with an O-ring at the distal end 3*d*. Alternatively, a threaded interface between proximal end 3*c* and distal end 3*e* is provided. During assembly, the capsule can be filled with coupling medium, for example by submersion of the position stabilizing structure 3 in a reservoir filled with the coupling medium and attaching the distal end 3*d* inside the reservoir.

The position stabilizing structure 3 can be made of rigid or soft biomedical grade material or a combination of both. For example, the proximal end 3*c* and the distal end 3*d* can be fabricated of PMMA, polycarbonate, polyethylene, polyurethane, polyimide, Pebax® or metal, e.g. stainless steel or titanium. Preferably, the proximal end 3*c* and the distal end 3*d* are connected by supporting structures 3*e*, which are preferably made of the same material.

As shown in FIG. 2, the imaging window 3*c*' is preferably located in a region of a circumference of the position stabilizing structure 3. The imaging window 3*c*' is preferably optically and acoustically transparent, and its thickness can be designed to decrease its influence on the imaging properties. For example, the imaging window 3*c*' can be tilted, drafted, wedged or coated with antireflective film to reduce backreflection of electromagnetic radiation. Additional marks or irregularities, for example providing orientational and/or positional information for evaluation during imaging, can be added in a region of the imaging window 3*c*'.

The imaging window 3*c*' can also be made of a flexible material which extends if the pressure inside the position stabilizing unit 3 is increased, such that the outer face 3*a* contacts the surrounding object. This further promotes stabilization and/or orientation of the imaging unit 2 relative to the object and improves acoustic coupling. Materials which are particularly suitable for the imaging window 3*c*' are all medical grade materials which have acoustic impedance close to tissue and water, i.e. optimally between 1 and 2 MRayls, and which have a low acoustic and optical attenuation coefficient. For example, polyurethane, polyethylene, RTV, ecothane, ethyl vinyl acetate, styrene butadiene, dimethyl pentene polymer or technogel are suitable. Preferably, the imaging window 3*c*' is covered with a thin, e.g. at most 50 μm thick, polyurethane foil. Alternatively, the imaging window 3*c*' is not sealed.

The radiation source 10, e.g. a pulsed or amplitude modulated tunable or single wavelength laser, a LED, a SLD or a laser diode, is optically coupled into the connecting element 9 at a proximal end of the connecting element 9. The connecting element 9 comprises a transmitting unit 11 configured to guide electromagnetic radiation generated by the radiation source 10 from the proximal end of the connecting element 9 to the distal end of the connecting element 9, in particular to the irradiation unit 6. For example, the transmitting unit 11 comprises a channel for free beam propagation or an optical fiber.

The irradiation unit 6 at the distal end of the connecting element 9 is configured to irradiate the region of interest to be imaged with the guided electromagnetic radiation, e.g. visible or infrared light. To this end, the illumination unit 6 comprises an optical arrangement and/or component configured to direct the light towards a field of view 8*b* of the detection unit 8, in particular into a field of view 8*b* of the at least one ultrasound transducer. This is achieved, e.g., by means of one or more micro-mirrors, prisms, or total internal reflection.

The field of view 8*b* of the at least one ultrasound transducer may comprise a focus 8*a*, e.g. a focus spot, focus line or focus area or region, from which acoustic waves generated in response to irradiation of the region of interest with electromagnetic radiation are detected with particularly high sensitivity and, hence, high signal-to-noise ratio. Alternatively, the detection unit 8 and/or the at least one ultrasound transducer may exhibit a non-focused field of view 8*b*, e.g. a divergent or parallel or cylindrical field of view (not shown).

Likewise, in some embodiments where the device for endoscopic optoacoustic imaging is further configured for ultrasound imaging, the field of view 8*b* of the detection unit 8 and/or the at least one ultrasound transducer may be focused or non-focused, so that ultrasound waves generated by the at least one ultrasound transducer are emitted into and, after being reflected, detected from an accordingly shaped, e.g. focused, divergent or parallel, field of view 8*b*.

In some embodiments, the irradiation unit 6 is also configured to receive electromagnetic radiation emanating from the tissue, for example in reaction to irradiating the tissue with electromagnetic radiation, and couple the received electromagnetic radiation into the transmitting unit 11 for being guided to the processing unit 4 provided at the proximal end of the connecting element 9 for further processing, in particular image generation.

The detection unit 8 of the imaging unit 2 is configured to detect optoacoustic responses from tissue irradiated with the electromagnetic radiation. Preferably, the surface of the at least one ultrasound transducer of the detection unit 8 is manufactured of a minimally light absorbing material and/or coated with a highly reflecting material such as gold or silver. Such a coating is advantageous because it can prevent that light backscattered from the region of interest creates an undesired optoacoustic signal at the transducer surface which might superpose and mask the (real) optoacoustic signal generated in the tissue. This is particularly advantageous in endoscopic applications where the region of interest is typically very close to the detection unit 8. The at least one ultrasound transducer may further comprise an acoustic matching layer to reduce acoustic impedance mismatches between the coupling medium and the at least one ultrasound transducer, thus improving transfer of the acoustic wave to the at least one ultrasound transducer.

The detection unit 8 can comprise a single ultrasound transducer or a multi-element ultrasound transducer array. In particular, multiple ultrasound transducers with different detection characteristics can be utilized in the detection unit 8 to access different penetration depths and image characteristics. For example, a high frequency transducer in combination with a low frequency transducer may be utilized, wherein the high frequency transducer provides high resolution information from superficial structures, whereas the low frequency transducer provides high penetration depth. Using multiple transducers may be beneficial because standard piezoelectric ultrasound detection technology does generally not provide ultra-broadband bandwidth characteristics preferably used in optoacoustic imaging to resolve different scales of sizes.

The at least one ultrasound transducer is preferably configured as a piezoelectric transducer, a micromachined transducer (CMUT) or an optical transducer using interferometric techniques for ultrasound wave detection. Moreover, the detection unit 2 preferably exhibits acoustic focusing properties to limit ultrasound detection to a narrow area, in particular a focus 8a, coinciding with an illumination pattern in the region of interest formed by the irradiation with electromagnetic radiation.

In the embodiment shown in FIG. 2, the irradiation unit 6 is arranged with respect to the detection unit 8 in a way such that the electromagnetic radiation is passing through an opening in the detection unit 8. By this means, an optimal overlap between the sensivity field of the at least one ultrasound transducer and the irradiation unit 6 can be achieved.

An amplification unit 12 amplifies the electrical signals generated by the at least one ultrasound transducer and matches the electrical impedance of the at least one ultrasound transducer to the transmitting unit 11, in particular an electrical wire, e.g. a microcoaxial cable, of the transmitting unit 11. It is advantageous to position the amplification unit 12 close to the at least one ultrasound transducer, because in this way the information in the detection signals generated by the at least one ultrasound transducer upon detection of ultrasound waves is conserved. Preferably, the amplification unit 12 is provided as an integrated circuit inside the at least one ultrasound transducer.

By means of the transmitting unit 11 the detection signals are guided from the detection unit 8 to the processing unit 4 provided at the proximal end of the connecting element 9, e.g. via electrical cable(s) or wirelessly. Preferably, an analog-to-digital converter may be provided, e.g. inside the position stabilizing unit 3, for converting analog detection signals into digital detection signals. Preferably, the analog-to-digital converter is configured to transmit the analog and/or digital detection signals from the detection unit 8 to the outside, in particular to the processing unit 4. Alternatively or additionally to the analog-to-digital converter, a signal transmission unit (not shown) may be provided, which is configured to transmit the analog and/or digital detection signals from the detection unit 8 to the outside, in particular to the processing unit 4. Preferably, the analog and/or digital detector signals are transferred wirelessly, e.g. via a WLAN or WiFi network. The processing unit 4 preferably comprises an ultrasound controller, in particular an amplifier and/or a filter, for amplifying and/or filtering the received detection signals and/or a reconstruction unit (not shown) configured to reconstruct high-quality optoacoustic images based on the, optionally amplified and/or filtered, detection signals. The reconstructed images can be outputted by an output unit 4a, for example a computer screen.

Preferably, the imaging unit 2 can be moved, in particular rotated and/or translated, by transmitting mechanical energy, i.e. forces or torques, from a drive unit 13 disposed at a proximal end of the connecting unit 9 to a carrier unit 16, on which the irradiation unit 6 and the detection unit 8 are mounted. To this end, the connecting element 9 preferably comprises a further transmitting unit 14, for example a driveshaft, in particular a torque coil. In the present embodiment shown in FIG. 2, the connecting element 9, for example a catheter, forms a hollow tube in which the driveshaft is disposed. Preferably, the driveshaft and/or the inside of the connecting element 9 is or are PTFE-coated for minimizing friction during rotation and/or translation of the driveshaft relative to the connecting element 9.

Preferably, the imaging unit 2, in particular the carrier unit 16, is designed to prevent the generation of turbulence in the coupling medium surrounding the imaging unit 2 upon rotation of the imaging unit 2, in particular the carrier unit 16. In particular, the carrier unit 16 and/or the imaging unit 2 preferably has a substantially circular shape, in particular a substantially circular outer surface exhibiting no protrusions. By this means, the carrier unit 16 and/or the imaging unit 2 can be rotated without displacing significant amounts of coupling medium, therefore minimizing turbulence and hence improving imaging quality.

The transmitting unit 14 is preferably coupled to the transmitting unit 11, in particular to an optical fiber and/or an electrical wire, such that the transmitting unit 14 and the transmitting unit 11 rotate synchronously, along with the imaging head on the carrier unit 16. Preferably, the transmitting unit 11 is centered inside the transmitting unit 14 with respect to the axis of rotation of the transmitting unit 14. In particular, an optical fiber may be centered on the axis of rotation of the transmitting unit 14 and an electrical wire may be wound around the optical fiber.

Two-dimensional imaging and three-dimensional imaging may be performed by irradiating the region of interest with a specific pattern and detecting the optoacoustic responses at specific locations. Preferably, the irradiation unit 6 and the detection unit 8 are oriented substantially perpendicular to the longitudinal axis 24 of the position stabilizing unit 3. By rotating or translating the optoacoustic imaging head around or along the longitudinal axis 24, respectively, using the transmitting unit 14, two-dimensional images are acquired. By combining both rotation and translation of the optoacoustic imaging head, volumetric scans, i.e. three-dimensional images, are acquired without moving the connecting element 9.

A typical translational scanning range is between 1 mm and 10 mm. Other translational scanning ranges are also possible, depending on the size of the position stabilizing structure 3. To avoid movement of the position stabilizing structure 3 and the connecting element 9 due to the rotational and translational force transmitted via the transmitting unit 14, the connecting element 9 is preferably configured such that it is resistant with respect to torsion, stretching and compression, while still providing sufficient flexibility and bending for insertion inside luminal organs.

Positional information of the imaging unit 2, in particular with respect to the position stabilizing unit 3 and/or the region of interest, is preferably obtained by the processing unit 4 from the drive unit 13. The processing unit 4 preferably uses the acquired detection signals and positional information to compute the two-dimensional and/or three-dimensional optoacoustic images, which can be outputted by output unit 4a in real-time. This is advantageous, e.g., during operations for visualization and analysis. In some embodiments, the processing unit 4 is configured to generate optoacoustic images using three dimensional rendering, allowing a more accurate representation of the anatomical structure. Preferably, the image generation is based on positional information of the distal end of the connecting element 9, which is obtained by tracking the location of the distal end of the connecting element 9 or the position stabilizing structure 3 relative to the region of interest which is imaged, or by tracking the position of the imaging unit 2 with respect to the position stabilizing structure 3.

Preferably, in order to couple the radiation generation unit 10 and/or processing unit 4 to the connecting unit 9, in particular to at least one of the transmitting units 11, 14, a rotary junction 15 is disposed at the proximal end of the connecting unit 9. The rotary junction 15 serves as an interface between a stationary part, i.e. the radiation generation unit 10 and the processing unit 4, and a rotating and/or translating part of the imaging device, i.e. the transmitting units 11, 14 and/or the imaging unit 2. Such rotary junction 11 allows to a couple light and/or electrical signals from the rotating part to the stationary part with minimal losses. By this means, the drive unit 13, for example an electric motor, can provide the torque for rotation and the pull/push force for translation or the imaging unit 2 via the rotary junction 15. The connecting element 9, in particular the transmitting units 11, 14, can be attached to the rotary junction 15 for example with a hybrid connector.

To enable clinical viable imaging rates, a rotation rate of the imaging unit 2 generated by the transmitted torque is preferably above 1 Hz, in particular above 10 Hz, and the electromagnetic radiation is pulsed at high rates, i.e. such above 1 kHz, in particular above 10 kHz. Moreover, the electromagnetic radiation can be intensity modulated with a complex periodic envelope at substantially high repetition rates, such as greater than 1 kHz, in particular above 10 kHz. A typical spectral range, at which the electromagnetic radiation may be provided in, ranges from 450 nm to about 980 nm. However, embodiments of the present invention may operate within other spectral windows. For instance, irradiation in the ultraviolet region, i.e. between 180 nm and 400 nm, where DNA and RNA show strong absorption, can be used for imaging of cell nucleons. Alternatively, irradiation in the near-infrared region, i.e. between 700 nm and 1400 nm, lipids, collagen and water can be imaged. Electromagnetic radiation at different selected wavelengths within the chosen spectral range can be delivered to the region of interest at different times, thereby providing acoustic signals proportional to the absorption at each respective wavelength. The detection signal corresponding to each wavelength can be processed to generate an optoacoustic image of the energy absorption in the tissue at the specific wavelength. The image may be further processed to obtain the absorption coefficient at the given wavelength.

FIG. 3 shows a second example of an imaging unit 2 disposed inside a position stabilizing structure 3, wherein an irradiation unit 6 and a detection unit 8 are mounted on a carrier unit 16 which is configured to be rotated and/or translated in an interior 3b *of the position stabilizing structure.*

The carrier unit 16 is coupled to a connecting element 9 for connecting the irradiation unit 4 and the detection unit 8 to a radiation source and a processing unit (see FIG. 2). To this end, the connecting element 9 comprises a transmitting unit 11 configured to relay electromagnetic radiation and/or electric signals, in particular detection signals generated by the detection unit 8. The connecting element 9 further comprises a transmitting unit 14 configured to transmit torque and/or a force from a drive unit (see FIG. 2) provided at a proximal end of the connecting element 9, wherein the transmitting unit 14 is rotatably arranged inside the static connecting element 9 and surrounds the transmitting unit 11 arranged in its center.

The irradiation unit 4 and the detection unit 8, which form an optoacoustic imaging head, are preferably rigidly connected to the transmitting unit 14 and/or to each other via the carrier unit 16, such that optical components, acoustic components, transmitting unit 11 and transmitting unit 14 are in a fixed position with respect to each other.

In order to secure the position stabilizing structure 3 at a distal end of the connecting element 9, the connecting element 9 preferably comprises a collar 9a, e.g. fabricated of a metal, at its distal end. The collar 9a acts as an anchor to avoid pulling out the connecting element 9 from the position stabilizing structure 3.

The carrier unit 16, which preferably forms a housing for the irradiation unit 6 and the detection unit 8, can further have a protruding structure 16a collinear to the longitudinal axis 24 of the position stabilizing structure 3, in particular the rotational axis of the transmitting unit 14. This protruding structure 16a is preferably configured to be inserted into a recess 3d' provided at a distal end 3d of the position stabilizing structure 3. In particular, the protruding structure 16a is configured to stabilize the rotational movement and/or translational movement of the carrier unit 16.

In order to facilitate a uniform rotation and/or translation of the optoacoustic imaging head, the carrier unit 16 is fabricated of a material with very low friction coefficient, e.g. PTFE, in particular at position where it engages the position stabilizing structure 3. Alternatively or additionally, a lubricant or a ball-bearing ring is used for rotational decoupling between the position stabilizing structure 3 and the carrier unit 16. In some embodiments, a washer 16b, preferably fabricated of PTFE, is threaded over the transmitting unit 14 and/or connected to the carrier unit 16 to separate the rotating optoacoustic imaging head from a proximal end 3c of the position stabilizing structure 3, in particular the static collar 9a.

The proximal end 3c preferably comprises an opening to facilitate assembling of the position stabilizing structure 3 with the connecting element 9. In order to prevent the connecting element 9 from kinking close to its connection with the position stabilizing structure 3, a strain relief tail 3f can be disposed at the proximal end 3c. At least a part of the tail 3f is shaped such that the shape of the position stabilizing structure 3 is matched, to facilitate a smooth transition between the shape of the position stabilizing unit 3 and the connecting element 9. The tail 3f can be made of urethane, nylon and/or another medical grade polymer. The tail 3f can be also shaped from epoxy and/or be epoxied to the proximal end 3c and the connecting element 9. Preferably, the tail 3f is shaped as to allow attachment to the accessory channel of a video-endoscope.

For further details, e.g. regarding the illumination unit 6, the detection unit 8 and the position stabilizing structure 3, the above elucidations with respect to the examples shown in FIGS. 1 and 2 apply accordingly.

FIG. 4 shows an example of a multimodal imaging unit 2 comprising an optoacoustic imaging unit, which, i.a., comprises an irradiation unit 6 and a detection unit 8, and an optical imaging unit, in particular an optical sensor 17. Preferably, both the optoacoustic imaging unit and the optical imaging unit are mounted on common carrier unit 16, which may be configured to form a housing, in particular a closed and/or liquid-tight housing, for components of the imaging unit 2. For example, the carrier unit 16 may comprise a first face 16a and a second face 16b, wherein the detection unit 8 is mounted on the first face 16a of the carrier unit 16 and the optical sensor 17 is mounted on the second face 16b of the carrier unit 16.

In present embodiment, a transmitting unit 14, which is configured to transmit a torque from a drive unit (see FIG. 2) provided at a proximal end of a connecting element 9, is connected to the carrier unit 16. A transmitting unit 11, preferably comprising an optical fiber 11a and an electrical wire 11b, is located inside the transmitting unit 14. Preferably, a part of the transmitting unit 11, in particular the optical fiber 11a, is decoupled from the transmitting unit, such that the transmitted torque and/or force is not applied to, i.e. does not act on, the optical fiber 11a.

Electromagnetic radiation emanating from the distal end of the optical fiber 11a passes through a beam shaping element 6a, e.g. a lens, and is reflected by a reflection element 6b. Preferably, the reflection element 6b is arranged in a 45° angle with respect to a longitudinal axis 24 of the position stabilizing structure 3, such that the electromagnetic radiation is guided through an opening of the detection unit 8. To ensure a liquid-tight sealing of the interior of the carrier unit 16, an optically transparent seal 16d is preferably provided on the detection unit 8 to seal the opening of the detection unit 8 in a liquid-tight manner.

A washer 16b, preferably fabricated of PTFE or other material with a low friction coefficient, is connected to a distal end of the transmitting unit 11, in particular to the optical fiber 11a, and configured to at least partially engage into a groove 16c of the carrier unit 16. By this means, the distance between the distal end of the optical fiber 11a or the beam shaping element 6a, respectively, and the reflection element 6b is kept constant. Therefore, the optical fiber 11a translates together with the carrier unit 16 along a longitudinal axis 24 of the position stabilizing structure 3, while being rotationally decoupled from the transmitting unit 14.

Preferably, electrical signals generated by the detection unit 8 in response to the detection of ultrasound waves are amplified by an amplification unit 12 and transmitted via the electrical wire 11b, e.g. a microcoaxial cable, to a processing unit (see FIG. 2) provided at a proximal end of the connecting element 9. The electrical wire 11b is disposed inside of the transmitting unit 14 and arranged and/or configured to rotate together with the transmitting unit 14, in particular connected to the transmitting unit 14 to avoid coiling around the stationary optical fiber 11a during rotation.

The optical sensor 17, for example a camera, comprises one or more light sources 17a. The reflection element 6b is preferably configured also to reflect electromagnetic radiation emitted from the light sources 17a through an optically transparent window 16e of the carrier unit 16 provided opposite to the detection unit 8. Vice versa, electromagnetic radiation emanating from the region of interest in response to the irradiation with electromagnetic radiation from the light sources 17a is reflected back to the optical sensor 17 such that an optical image of at least a part of the region of interest can be acquired, wherein the optical image shows an area of the region of interest opposite to an area from which an optoacoustic image is acquired based on the detection signals generated by the detection unit 8. Preferably, the optical sensor 17 is connected to the carrier unit 16, such that upon rotation of the carrier unit 16, the complete region of interest surrounding the position stabilizing unit 16 can be imaged by the imaging sensor 17.

Preferably, the imaging unit 2 and/or the carrier unit 16 can be moved inside the position stabilizing structure 3 along a helical path, such that volumetric scans of the region of interest can be obtained without moving the position stabilizing structure 3 with respect to the region of interest. The so-called helical scanning is preferably implemented by using two complementary threads, wherein a first thread 18a is disposed at the transmitting unit 14 and a complementary second thread 18b is disposed at the position stabilizing structure 3, in particular at a proximal end thereof. When applying torque via the transmitting unit 14 to the carrier unit 16, the carrier unit 16 is forced by the first and second thread 18a, 18b to perform a helical movement with respect to the position stabilizing structure 3. The pitch of the threads 18a, 18b determines how far the carrier unit 16 translates along the longitudinal axis 24 of the position stabilizing structure 3 per rotation.

A continuous movement of the carrier unit, and thereby a continuous scan of the region of interest by the imaging unit 2, in particular the detection unit 8 and/or the optical sensor 17, is preferably achieved by periodically changing the direction of the torque applied to the transmitting unit 14. To this end, the transmitting unit 14 preferably comprises a multilayer torque coil, which consists of two wires coiled in opposite direction, such that torque can be transmitted both in clockwise and counterclockwise direction.

A combination of helical movement of the carrier unit 16 inside the position stabilizing unit 3 and a movement of the position stabilizing unit 3 along the region of interest can be done to image large areas.

The above described embodiment can be used as a standalone device or as an extension to a conventional video-endoscope, to provide the latter with an additional optoacoustic imaging modality. Since the position stabilizing structure 3 usually has a larger diameter than the diameter of accessory channels of the video-endoscope and thus does not fit through the accessory channels, the proximal end of the connecting unit 9 is designed to allow back-loading of the video-endoscope. By this means, the clinical workflow can be matched.

In an alternative embodiment, the drive unit (not shown) may be disposed in the interior 3b of the position stabilizing unit 3 and directly and/or via a drive shaft and/or a threaded rod connected to and/or coupled with the carrier unit 16. Preferably, the threaded rod, which is driven by the driving unit, engages a threaded hole provided or fixed at the position stabilizing unit 3. The engaging threaded rod and threaded hole act similarly to the first and second threads 18a, 18b of the example described above. Therefore, also with present embodiment the carrier unit 16 can be moved inside the position stabilizing structure 3 along a helical path, such that volumetric scans of the region of interest can be obtained without moving the position stabilizing structure 3 with respect to the region of interest.

In another alternative embodiment (not shown), the optoacoustic imaging head allows parallel imaging in two directions. In this case, the detection unit 8 comprises at least two ultrasound transducers oriented in opposite directions perpendicular to the longitudinal axis 24 of the position stabilizing unit 3, in particular on two opposite faces of the carrier unit 16. Further, the electromagnetic radiation is guided in these directions by providing an according reflection element 6b, in particular a triangular optical element, e.g. a prism. The parallel imaging helps speeding up the imaging process, because per pulse of electromagnetic radiation, a multitude of optoacoustic signals could be acquired.

FIG. 5 shows an example of a backend 19 of a device for endoscopic optoacoustic imaging, wherein the backend 19 is coupled to a proximal end of a connecting element 9, which connects the backend 19 with an imaging head (see FIG. 2) at the distal end of the connecting element 9.

A processing unit 4 of the backend 19 is configured to control an optoacoustic module 4b comprising a radiation source 10 and an ultrasound driver 8b, in particular an amplifier and/or filter, for processing detection signals generated by a detection unit (see FIG. 2).

In present example, the processing unit 4 is further configured to control an optical coherence tomography module 4c comprising an interferometer 20 and/or an imaging module 4d comprising optical sensor drivers and/or and/or light source drivers 25 for controlling one or more optical sensors or light sources provided at the imaging head, respectively.

Additionally or alternatively, the processing unit 4 may be configured to control a reflectance spectroscopy module 4e comprising a second radiation source 10a and first light detection and filtration electronics 21a and configured to perform reflectance spectroscopy and/or a fluorescence module 4f, comprising a third radiation source 10b and second light detection and filtration electronics 21b and configured to perform fluorescence imaging.

The radiation sources 10, 10a, 10b, the interferometer 20 and the light detection and filtration electronics 21a, 21b are preferably coupled via a beam splitter 22 or dichroic mirror to an optical fiber 11a arranged in the center of the connecting element 9. Due to said coupling, the optical fiber 11a is fixed with respect to the connecting element 9.

The ultrasound driver 8a and the imaging module 4d are coupled via a rotary junction 15 to electrical wires 11b running along the optical fiber 11a through the connecting element 9. By that means, the electrical wires 11b are arranged to rotate synchronous with a first transmitting element 14 configured to transmit a torque generated by a drive unit 13 to an imaging head at the distal end of the connecting element 9. In particular, the electrical wires 11b are connected to the first transmitting element 14.

Preferably, the rotatable first transmission unit 14 and the electrical wires 11b connected thereto are designed to surround the static optical fiber 11a. This arrangement of first transmission unit 14, electrical wires 11b and optical fiber 11a is preferably arranged in a first channel 22a of the connecting element 9, wherein channel walls, the first transmission unit 14 and/or the optical fiber 9 may be coated with PTFE to reduce friction. Alternatively or additionally, a lubricant may be filled into the first channel 22a.

The optical fiber 11a may include a plurality of optical transmission channels. For example, in some embodiments, the optical fiber 11a may be designed as a double clad fiber. The double clad fiber preferably comprises a small diameter core, in particular a single mode core, and a multi-mode inner cladding, which may be arranged concentrically around the single mode core. Preferably, the single mode core transmits OCT signals, i.e. electromagnetic radiation, from the proximal end to the distal end and/or from the distal end to the proximal end. Additionally or alternatively, the inner core may transmit electromagnetic radiation, in particular illumination light, for optoacoustic, fluorescence and/or other optical imaging modalities from the proximal end to the distal end of the optical fiber 11a or vice versa. Additionally or alternatively, the multi-mode inner cladding may transmit electromagnetic radiation, in particular illumination light, for optoacoustic, fluorescence and/or other optical imaging modalities from the proximal end to the distal end of the optical fiber 11a or vice versa. In particular, the multi-mode inner cladding may transmit electromagnetic radiation emanated from the region of interest in response to the irradiation with the electromagnetic radiation from the distal end to the proximal end of the optical fiber 11a.

Preferably, in present example the connecting element 9 comprises a second channel 22b configured to convey a coupling medium from the proximal end of the connecting element 9 into the position stabilizing unit (see FIGS. 1 to 4) provided at the distal end of the connecting element 9 or vice versa.

In another embodiment, the connecting element 9 may comprise a further channel (not shown) in communication with the exterior of the position stabilizing unit 3. By this means, coupling medium can be guided into the space surrounding the position stabilizing unit 3, in particular into a lumen, e.g. a hollow organ, such that optical and/or ultrasound coupling can be established between the region of interest, e.g. the wall of the hollow organ, and the position stabilizing structure 3.

The coupling medium is preferably configured to facilitate transmission of the electromagnetic radiation between irradiation unit 6 and region of interest as well as ultrasound waves between region of interest and detection unit 8 with no or at least minimal absorption of the ultrasound waves and/or electromagnetic radiation and no distortion of their propagation direction. Preferably, the coupling medium exhibits an acoustic impedance value close to the acoustic impedance of tissue (~1.6 Mrayl), i.e. it may be between 1 and 2 Mrayl and preferably is between 1.2 Mrayl and 1.8 Mrayl, in order to maximize transmission of energy of the acoustic waves. The coupling medium may be a fluid so as to fill all available spaces between detection unit 8 and region of interest and avoid air gaps. In liquid form, the coupling medium can also be used as a means for inflating or deflating the at least partially elastic position stabilizing unit, for instance for adapting it to the shape of a surrounding lumen. Additionally, the coupling medium is preferably non-scattering and transparent for electromagnetic radiation at wavelengths used in optoacoustic imaging and other optical imaging modalities. For transmitting electromagnetic radiation in the visible range (e.g. 400-700 nm), water may be a suitable coupling medium being transparent, having an acoustic impedance of ~1.5 Mrayl and an optical absorption coefficient below 0.01 $cm^{-1}$. When transmitting electromagnetic radiation in the near-infrared range, in particular above 850 nm, heavy water ($D_2O$) may be a preferred coupling medium as it has a significant lower optical absorption coefficient than water at the corresponding wavelengths. Heavy water may also be suited as a coupling medium optoacoustic imaging in conjunction with OCT, which typically uses light in the wavelength range above 1000 nm (e.g. 1060 nm, 1300 nm, 1700 nm etc.).

Alternatively or additionally, the coupling medium provides lubrication and, in contrast to conventional clinical ultrasound applications, a low viscosity for facilitating movement, in particular rotation, of the carrier unit 16 or imaging head mounted thereon, and prevent the generation of air bubbles. Preferably, Silicone oil is used as a low viscosity couplant for ultrasound, but water and heavy water also have suitable characteristics. Preferably, the coupling medium comprises an additional preservative hindering the growth of microorganisms, especially bacteria and fungi, while preserving or improving the acoustic properties. For instance, alcohol is a suitable preservative, but other substances may be also possible.

Preferably, the coupling liquid is biocompatible and may be applied, e.g. instilled, directly into the space surrounding the position stabilizing unit 3, in particular into the imaged lumen. Based on the signals, in particular the detection signals, provided by the optoacoustic module 4b, the optical coherence tomography module 4c, the imaging module 4d, the reflectance spectroscopy module 4e and/or the fluorescence module 4f the processing unit 4 generates according images and displays them on an output unit 4a. For example, an optical camera image 23a of a lumen of an object, into which the imaging head at the distal end of the connecting element 9 has been inserted, may be displayed along with an optoacoustic image 23b and an optical coherence tomography image 23c, wherein the latter two images 23b, 23c show a cross-section of the camera image 23a of the lumen in real-time. Alternatively or additionally, hybrid images may be generated by fusioning image information contained in at least two images which were acquired by different imaging modalities.

Multimodal imaging may be done sequentially or in parallel. Sequential imaging includes that one modality acquires one of a 1D, 2D or 3D image before another modality acquires one of a 1D, 2D or 3D image, i.e. imaging is done in a time-shared fashion. Parallel means that at least two modalities acquire images simultaneously.

FIG. 6 shows an example of an amplification unit 12 configured to be at least partially disposed inside a position stabilizing structure and to amplify detection signals generated by a detection unit before transmission through a transmitting unit 11 (see FIGS. 2 to 5). This is advantageous because the detection signals are usually weak and thus prone to electromagnetic disturbance from any external interfering source.

The detection signal from the detection unit enters the amplification unit 12 at IN. Blocking capacitors $C_{block}$ prevent DC biasing signals from coupling into the detection unit or the output of the amplification unit 12, respectively. In the case of a detection unit comprising a piezoelectric or CMUT sensor, no blocking capacitor $C_{block}$ is needed, since the sensor by its nature has a capacitive behavior. The second transmitting element 11 transmits the detection signal and conveys a DC supply voltage to the amplification module 12a. A blocking inductance RFC impedes higher frequency signals from reaching the power supply $V_{00}$. Bypass capacitor $C_{bypass}$ bypasses any left AC components to the ground. The amplified detection signals is output at OUT.

Preferably, some of the components of the amplification unit, in particular the power supply $V_{00}$, the blocking inductance RFC and a blocking capacitor $C_{block}$, are part of an ultrasound driver (see FIG. 5), i.e. disposed outside the position stabilizing structure. By this means, the number of parts, in particular conventional electrical components, of the amplification unit 12 remaining inside the position stabilizing structure may be minimized. Further, the transmission of the detection signals as well as the DC power supply voltage for the amplification unit 12 may be relayed from the amplification unit 12 to the ultrasound driver or from a power supply to the amplification unit 12, respectively, by the same transmission line, e.g. a second transmitting unit.

FIG. 7 shows another example of an imaging unit 2 disposed in the interior of a position stabilizing structure 3. In distinction to the example described above with reference to FIG. 2, a drive unit 13, e.g. an electrical motor, is provided in the interior 3b of the position stabilizing structure 3, so that an additional transmission unit 14 (as shown in FIG. 2), e.g. a torque coil, for transmitting a torque from a driving unit provided outside the position stabilizing structure 3 is dispensable.

In present example, the position stabilizing structure 3 comprises a, preferably rigid, proximal end structure 3c and a, preferably rigid, distal end structure 3d, wherein the proximal end structure 3c and the distal end structure 3d are arranged along the longitudinal axis 24 of the position stabilizing structure 3. As indicated in the figure, the driving unit 13 is preferably disposed at or in the region of the proximal end structure 3c in the interior 3b of the position stabilizing structure 3. Providing the driving unit 13 at the proximal end structure 3c of the position stabilizing structure 3 has the advantage that conducting wires for electrical power supply of the driving unit 13 have to be laid only up to the proximal end 3c of the position stabilizing structure 3, making wires running through the position stabilizing structure 3, in particular through a region where the imaging unit 2 is positioned and/or towards the distal end structure 3d of the position stabilizing structure 3, dispensable. This allows for a stable full 360° rotational scan of the imaging unit 2 which is not disturbed and/or adversely affected by conducting wires crossing the position stabilizing structure 3 and/or the field of view of the imaging unit 2.

Regarding further components, aspects and advantages of the example shown in FIG. 7, the above description with reference to FIG. 2 applies accordingly.

The invention claimed is:

1. A device for endoscopic optoacoustic imaging, the device comprising:
   an imaging unit configured to be at least partially inserted into an object, the imaging unit comprising:
   an irradiation unit configured to irradiate a region of interest inside the object with electromagnetic radiation, and
   a detection unit comprising at least one ultrasound transducer configured to detect ultrasound waves generated in the region of interest in response to irradiating the region of interest with the electromagnetic radiation and to generate detection signals, the at least one ultrasound transducer exhibiting a field of view being at least partially located in the irradiated region of interest,
   a position stabilizing structure forming a housing for at least a part of the imaging unit, the position stabilizing structure comprising an outer face and an interior and being configured to stabilize and/or fix the imaging unit in a position and/or orientation in the object by bringing the outer face of the position stabilizing structure into contact with the object,
   a processing unit configured to generate an optoacoustic image of the region of interest based on the detection signals; and
   a carrier unit disposed in the interior of the position stabilizing structure, the carrier unit comprising a proximal end, a distal end, a first lateral face, and a second lateral face, wherein the irradiation unit and the detection unit are mounted on the carrier unit such that the electromagnetic radiation emanating from the irradiation unit is directed towards the field of view of the at least one ultrasound transducer, the detection unit being mounted on the first lateral face and being oriented substantially perpendicular to a longitudinal axis of the position stabilizing unit, the at least one ultrasound transducer exhibiting a sensitive surface, wherein the at least one ultrasound transducer is mounted and/or arranged on the carrier unit such that the sensitive surface of the ultrasound transducer faces towards the region of interest inside the object, wherein the at least one at least one ultrasound transducer comprises an aperture or window section being at least partially transparent to the electromagnetic radiation; and an optical fiber and a reflection element, wherein a distal end of the optical fiber is disposed within the carrier unit between the proximal end of the carrier unit and the reflection element, wherein the reflection element is arranged within the carrier unit between the distal end of the optical fiber and the ultrasound transducer and is configured to reflect the electromagnetic radiation emanating from the distal end of the optical fiber such that the reflected electromagnetic radiation passes through the aperture or window section of the ultrasound transducer to irradiate the region of interest inside the object.

2. The device according to claim 1, wherein the carrier unit is configured to be rotated and/or translated with respect to the position stabilizing structure around and/or along a rotational-translational axis such that the region of interest is scanned by the field of view of the at least one ultrasound transducer upon a rotation and/or translation of the carrier unit with respect to the position stabilizing structure.

3. The device according to claim 2, wherein the field of view of the at least one ultrasound transducer runs substantially perpendicularly to the rotational-translational axis.

4. The device according to claim 3 comprising at least one of:
a first transmitting unit configured to transmit at least one of a torque or force to the carrier unit such that the carrier unit is at least one of rotated around or translated along the rotational-translational axis with respect to the position stabilizing structure, or
a driving unit configured to rotate the carrier unit at least one of around or to translate the carrier unit along the rotational-translational axis with respect to the position stabilizing structure.

5. The device according to claim 4, wherein
the position stabilizing structure comprises a first thread and the at least one of the first transmitting unit or the driving unit comprises a second thread which is complementary to the first thread and mechanically coupled with the carrier unit, wherein the first thread and the second thread are in thread engagement, so that at least one of by applying a torque to the first transmitting unit or by activating the driving unit the second thread is rotated, whereby the carrier unit is rotated and translated simultaneously with respect to the position stabilizing structure, whereby the field of view of the at least one ultrasound transducer moves through the region of interest along a helical pathway.

6. The device according to claim 3 comprising a driving unit disposed in the interior of the position stabilizing structure and configured to rotate the carrier unit around and/or to translate the carrier unit along the rotational-translational axis with respect to the position stabilizing structure.

7. The device according to claim 6, the position stabilizing structure further comprising a proximal end structure and a distal end structure, wherein the proximal end structure and the distal end structure are arranged along the longitudinal axis of the position stabilizing structure, and the driving unit is disposed in the interior of the position stabilizing structure.

8. The device according to claim 1, wherein the position stabilizing structure comprises a membrane which is transparent for the electromagnetic radiation and/or the ultrasound waves.

9. The device according to claim 8, the membrane being spanned between a proximal end structure and a distal end structure of the position stabilizing structure to form a hollow cylinder which is closed, at a base region, by the proximal end structure and, at a top region, by the distal end structure.

10. The device according to claim 8, the membrane being configured to adapt its shape and/or size to an interior of the object, such that an outer face of the membrane assumes a size and/or shape which at least partially meshes with the shape and/or size of the interior of the object, whereby the position stabilizing structure is fixed and/or locked inside the object at least partially due to form fit.

11. The device according to claim 1, the imaging unit further comprising an optical sensor disposed adjacent to the distal end of the carrier unit and configured to acquire an optical image of a part of the region of interest which is opposite to an area from which the optoacoustic image is acquired with respect to the reflection element, wherein an optically transparent window is provided at the second lateral face of the carrier unit, wherein the optical sensor comprises one or more light sources configured to emit an additional electromagnetic radiation through the optically transparent window.

12. The device according to claim 1, comprising an amplification unit disposed in the interior of the position stabilizing structure and configured to amplify the detection signals generated by the at least one ultrasound transducer.

13. The device according to claim 1, comprising at least one transmitting unit comprising a proximal end and a distal end and configured to guide electromagnetic radiation from at least one of the proximal end to the distal and and/or from the distal end to the proximal end, wherein the imaging unit further comprises at least one rotational junction configured to optically couple the distal end of the transmitting unit to the irradiation unit and/or the detection unit.

14. The device according to claim 1, comprising at least one transmitting unit comprising a proximal end and a distal end and configured to guide electrical signals from at least one of the proximal end to the distal and and/or from the distal end to the proximal end, wherein the imaging unit further comprises at least one rotational junction configured to electrically couple the distal end of the transmitting unit to the irradiation unit and/or the detection unit.

* * * * *